United States Patent
Jain (10) Patent No.: US 12,343,522 B2
(45) Date of Patent: Jul. 1, 2025

(54) IMPLANTABLE NEUROSTIMULATOR TO TREAT CHRONIC MIGRAINE HEADACHES

(71) Applicant: Shiratronics, Inc., Brooklyn Park, MN (US)

(72) Inventor: Mudit K. Jain, Santa Clara, CA (US)

(73) Assignee: Shiratronics, Inc., Brooklyn Park, MN (US)

( * ) Notice: Subject to any disclaimer, the term of this patent is extended or adjusted under 35 U.S.C. 154(b) by 730 days.

(21) Appl. No.: 17/434,161

(22) PCT Filed: Mar. 9, 2020

(86) PCT No.: PCT/US2020/021680
§ 371 (c)(1),
(2) Date: Aug. 26, 2021

(87) PCT Pub. No.: WO2020/185666
PCT Pub. Date: Sep. 17, 2020

(65) Prior Publication Data
US 2022/0168573 A1    Jun. 2, 2022

Related U.S. Application Data

(60) Provisional application No. 62/817,989, filed on Mar. 13, 2019.

(51) Int. Cl.
*A61N 1/05* (2006.01)
*A61N 1/36* (2006.01)
*A61N 1/372* (2006.01)

(52) U.S. Cl.
CPC ......... *A61N 1/0526* (2013.01); *A61N 1/0504* (2013.01); *A61N 1/36075* (2013.01)

(58) Field of Classification Search
CPC .............. A61N 1/36075; A61N 1/0504; A61N 1/0526; A61N 1/0551; A61N 1/37211; A61N 1/0476; A61N 1/0529
See application file for complete search history.

(56) References Cited

U.S. PATENT DOCUMENTS

2008/0132979 A1* 6/2008 Gerber ................. A61N 1/0526
607/116
2010/0004721 A1* 1/2010 Bryce ................. A61B 17/3468
607/116
(Continued)

FOREIGN PATENT DOCUMENTS

WO    WO-2017049292 A2    3/2017
WO    WO-2020185666 A1    9/2020

OTHER PUBLICATIONS

"International Application Serial No. PCT/US2020/021680, International Search Report mailed Jul. 3, 2020", 4 pgs.
(Continued)

*Primary Examiner* — Pamela M. Bays
*Assistant Examiner* — Christine Sison
(74) *Attorney, Agent, or Firm* — Schwegman, Lundberg & Woessner, P.A.

(57) ABSTRACT

A system may include one implantable pulse generator and at least one implantable lead. The pulse generator may include a processor, a driving system for driving electrodes, a communication circuit, and a housing configured to be subcutaneously implanted. The lead may be configured to extend from the pulse generator to at least one neural target on a left side of a head and a neural target on a right side of the head. The lead may include at least two electrode sets, each including at least two electrodes. The lead be configured to be used to subcutaneously place the at least two electrode sets near the at least two neural targets, respectively, and electrically connect the pulse generator to each of the at least two electrodes sets to enable the driving system to drive the at least two electrode sets to stimulate the at least two neural targets.

20 Claims, 5 Drawing Sheets

(56) References Cited

U.S. PATENT DOCUMENTS

| | | | | |
|---|---|---|---|---|
| 2011/0071540 A1* | 3/2011 | Kast | .................... | A61N 1/0551 |
| | | | | 606/129 |
| 2011/0112603 A1* | 5/2011 | Degiorgio | ............ | A61N 1/0492 |
| | | | | 607/45 |
| 2014/0371824 A1* | 12/2014 | Mashiach | .......... | A61N 1/36146 |
| | | | | 607/60 |
| 2015/0051678 A1* | 2/2015 | Reed | .................. | A61N 1/36075 |
| | | | | 607/116 |
| 2016/0331953 A1 | 11/2016 | Reed et al. | | |
| 2017/0035316 A1* | 2/2017 | Kuzniecky | ........... | A61B 5/0002 |

OTHER PUBLICATIONS

"International Application Serial No. PCT/US2020/021680, Written Opinion mailed Jul. 3, 2020", 5 pgs.
"International Application Serial No. PCT US2020 021680, International Preliminary Report on Patentability mailed Sep. 23, 2021", 7 pgs.
"European Application Serial No. 20716316.3, Response Filed Apr. 28, 2022 to Communication Pursuant to Rules 161(2) and 162 EPC mailed Oct. 20, 2021", 15 pgs.

* cited by examiner

IMPLANTABLE NEUROSTIMULATOR TO TREAT CHRONIC MIGRAINE HEADACHES

CLAIM OF PRIORITY

This is application is a U.S. National Stage Filing under 35 U.S.C. 371 from International Application No. PCT/US2020/021680, filed on Mar. 9, 2020, and published as WO 2020/185666 on Sep. 17, 2020 which claims the benefit of priority under 35 U.S.C. § 119(e) of U.S. Provisional Patent Application Ser. No. 62/817,989, filed on Mar. 13, 2019, which is herein incorporated by reference in its entirety.

TECHNICAL FIELD

This document relates generally to medical devices, and more particularly, but not by way of limitation, to systems, devices, and methods to devices, systems and associated methods for treating chronic headaches such as chronic migraine headaches.

BACKGROUND

The treatment of chronic migraine has been limited to a number of procedures, pharmacological procedures or neuro-stimulation procedures. With respect to the neuro-stimulation procedures, devices have been developed for implanting in association with electrode leads, such that the electrodes are disposed proximate to some particular neural structure in an individual. These implanted devices can have batteries associated therewith for powering the electrodes or they can be externally activated.

SUMMARY

This document discusses, among other things, systems and methods to treat chronic headaches. The use of a single pules generator to target more than one neural target around the head reduces surgical incisions and shortens the time to perform the implant procedure.

An example (e.g. "Example 1") of subject matter (e.g. a neurostimulator system) may include one implantable pulse generator and at least one implantable lead. The one implantable pulse generator may include a processor, a driving system for driving electrodes, a communication circuit, and an implantable device housing configured to contain the processor, the driving system and the communication circuit. The implantable device housing may be configured to be subcutaneously implanted. In some embodiments, the one implantable pulse generator may include at least one connector configured to connect to at least one implantable lead. In some embodiments, the at least one implantable lead is integrally formed with the implantable pulse generator (e.g. lead(s) integrally formed with the implantable device housing) to form a unibody structure. The at least one implantable lead may be configured to extend from the subcutaneously-implanted one implantable pulse generator to at least two neural targets. The at least two neural targets may include at least one neural target on a left side of a head and at least one neural target on a right side of the head. The at least one implantable lead may include at least two electrode sets. Each of the at least two electrode sets include at least two electrodes. The at least one implantable lead with the at least two electrode sets may be configured to be used to subcutaneously place the at least two electrode sets near the at least two neural targets, respectively, and electrically connect the one implantable pulse generator to each of the at least two electrodes sets to enable the driving system to drive the at least two electrode sets to stimulate the at least two neural targets including the at least one neural target on the left side of the head and the at least one neural target on the right side of the head.

In Example 2, the subject matter of Example 1 may optionally be configured such that the implantable device housing may be configured for implantation in a subcutaneous pocket superficial to the splenius capitis muscle or semispinalis capitis muscle or in a subcutaneous pocket superficial to the sternocleidomastoid muscle inferior to a mastoid process.

In Example 3, the subject matter of any one or any combination of Examples 1-2 may optionally be configured in some embodiments such that the at least two neural targets include at least two neural targets selected from the group consisting of: left supraorbital nerves, left temporal nerves, left occipital nerves, right supraorbital nerves, right temporal nerves and right occipital nerves.

In some embodiments, the subject matter of any one or any combination of Examples 1-2 may optionally be configured such that the at least two neural targets include at least two neural targets selected from the group consisting of: a greater occipital nerve (GON), a supraorbital nerve (SON), and a sphenopalatine ganglion (SPG).

In some embodiments, the subject matter of any one or any combination of Examples 1-2 may optionally be configured such that the at least two neural targets include at least two neural targets selected from the group consisting of: a facial nerve and a supraorbital nerve (SON).

In Example 4, the subject matter of any one or any combination of Examples 1-3 may optionally be configured such that the at least two neural targets include at least four neural targets, the at least four neural targets including left supraorbital nerves, left occipital nerves, right supraorbital nerves, and right occipital nerves.

In Example 5, the subject matter of any one or any combination of Examples 1-4 may optionally be configured such that the at least two neural targets include at least six neural targets, the at least six neural targets including: left supraorbital nerves, left temporal nerves, left occipital nerves, right supraorbital nerves, right temporal nerves and right occipital nerves.

Separate leads may be used to distribute the at least two electrode sets to the at least two neural targets. In Example 6, for example, the subject matter of any one or any combination of Examples 1-5 may optionally be configured such that the at least one implantable lead includes at least two implantable leads.

In Example 7, the subject matter of any one or any combination of Example 6 may optionally be configured such that the at least two implantable leads include a first lead and a second lead. The first lead may include at least one of the two electrode sets for subcutaneous placement on a left side of the head. The first lead may be configured to extend from the one implantable pulse generator to the left side of the head with the at least one of the two electrodes sets near at least one of the at least four neural targets. The second lead may include at least one of the two electrode sets for subcutaneous placement on a right side of the head. The second lead may be configured to extend from the one implantable pulse generator to the right side of the head with the at least one of the two electrode sets near at least one of the at least four neural targets.

In Example 8, the subject matter of any one or any combination of Examples 6-7 may optionally be configured such that the at least two electrode sets include at least four electrode sets. The first lead may include at least two of the at least four electrodes sets for subcutaneous placement on the left side of the head. The first lead may be configured to extend from the one implantable pulse generator to the left side of the head with the at least two of the at least four electrode sets near at least two neural targets, respectively, selected from the group consisting of: left supraorbital nerves, left temporal nerves, and left occipital nerves. The second lead may include at least two of the at least four electrodes sets for subcutaneous placement on the right side of the head. The second lead may be configured to extend from the one implantable pulse generator to the right side of the head with the at least two of the at least four electrode sets near at least two neural targets, respectively, selected from the group consisting of: right supraorbital nerves, right temporal nerves, and right occipital nerves.

In Example 9, the subject matter of any one or any combination of Examples 6-8 may optionally be configured such that the at least two electrode sets include at least six electrode sets. The first lead may include at least three of the at least six electrode sets for subcutaneous placement on the left side of the head. The first lead may be configured to extend from the one implantable pulse generator to the left side of the head with the at least three of the at least six electrode sets near the at least three left-side neural targets, respectively, the at least three left-side neural targets including left supraorbital nerves, left temporal nerves, and left occipital nerves. The second lead may include at least three of the at least six electrode sets for subcutaneous placement on the right side of the head. The second lead may be configured to extend from the one implantable pulse generator to the right side of the head with the at least three of the at least six electrode sets near the at least three right-side neural targets, respectively, the at least three right-side neural targets including right supraorbital nerves, right temporal nerves, and right occipital nerves.

Lead(s) may have distal branches used to distribute the at least two electrode sets to the at least two neural targets. In Example 10, for example, the subject matter of any one or any combination of Examples 1-5 may optionally be configured such that the at least one implantable lead includes at least one lead having at least two distal branches, the at least two electrode sets being distributed on the at least two distal branches.

In Example 11, the subject matter of Example 10 may optionally be configured such that the at least two distal branches include at least a first branch and at least a second branch. The at least the first branch may include at least one of the at least two electrode sets for subcutaneous placement on the left side of the head with the at least one of the at least two electrode sets near at least one of the at least two targets. The at least the second branch includes at least one of the at least two electrode sets for subcutaneous placement on the right side of the head with the at least one of the at least two electrode sets near at least one of the at least two neural targets.

In Example 12, the subject matter of any one or any combination of Examples 10-11 may optionally be configured such that the at least two electrode sets include at least four electrode sets. The at least the first branch may include at least two of the at least four electrode sets for subcutaneous placement on the left side of the head with the at least two of the at least four electrode sets near at least two neural targets, respectively, selected from the group consisting of: left supraorbital nerves, left temporal nerves, and left occipital nerves. The at least the second lead may include at least two of the at least four electrode sets for subcutaneous placement on the right side of the head with the at least two of the at least four electrode sets near at least two neural targets, respectively, selected from the group consisting of: right supraorbital nerves, right temporal nerves, and right occipital nerves.

In Example 13, the subject matter of any one or any combination of Examples 10-12 may optionally be configured such that the at least two electrode sets include at least six electrode sets. The at least the first branch may include at least three of the at least six electrode sets for subcutaneous placement on the left side of the head with the at least three of the at least six electrode sets near at least three left-side neural targets, respectively, where the at least three left-side neural targets may include left supraorbital nerves, left temporal nerves, and left occipital nerves. The at least the second branch may include at least three of the at least six electrode sets for subcutaneous placement on the right side of the head with the at least three of the at least six electrode sets near at least three right-side neural targets, respectively. The at least three right-side neural targets may include right supraorbital nerves, right temporal nerves, and right occipital nerves.

In Example 14, the subject matter of any one or any combination of Examples 10-13 may optionally be configured such that the at least two electrode sets include at least four electrode sets. The at least the first branch may include at least two left-side branches for subcutaneous placement on the left side of the head with at least two of the at least four electrode sets near at least two left-side neural targets, respectively. The at least two left-side neural targets may include at least two neural targets selected from the group consisting of: left supraorbital nerves, left temporal nerves, and left occipital nerves. The at least the second branch may include at least two right-side branches for subcutaneous placement on the right side of the head with at least two of the at least four electrode sets near at least two right-side neural targets, respectively. The at least two right-side neural targets may include at least two neural targets selected from the group consisting of: right supraorbital nerves, right temporal nerves, and right occipital nerves.

In Example 15, the subject matter of any one or any combination of Examples 10-14 may optionally be configured such that the at least two electrode sets include at least six electrode sets. The at least the first branch may include at least three left-side branches for subcutaneous placement on the left side of the head with at least three of the at least six electrode sets near left supraorbital nerves, left temporal nerves, and left occipital nerves, respectively. The at least the second branch may include at least three right-side branches for subcutaneous placement on the right side of the head with at least three of the at least six electrode sets near right supraorbital nerves, right temporal nerves, and right occipital nerves, respectively.

In Example 16, the subject matter of any one or any combination of Examples 10-15 may optionally be configured such that the at least two distal branches include at least one pair of branches, and the branches in the at least one pair of branches have an equal length.

In Example 17, the subject matter of any one or any combination of Examples 10-16 may optionally be configured such that the at least two distal branches include a first pair of branches and a second pair of branches. Each of the branches in the first pair of branches may have a first length, and each of the branches in the second pair of branches may have a second length different from the first length.

In Example 18, the subject matter of Example 17 may optionally be configured such that the at least two distal branches further include a third pair of branches. Each of the branches in the third pair of branches may have a third length different from the first length and the second length.

An example (e.g. "Example 19") of subject matter (e.g. a method for providing a therapy to treat pain) may include subcutaneously implanting one implantable pulse generator and subcutaneously implanting at least one implantable lead. The one implantable pulse generator may include a processor, a driving system for driving electrodes, a communication circuit, and an implantable device housing configured to contain the processor, the driving system and the communication circuit. The housing may be configured to be subcutaneously implanted. The at least one lead may be configured to extend from the subcutaneously-implanted one implantable pulse generator to at least two neural targets. The at least two neural targets may include at least one neural target on a left side of a head and at least one neural target on a right side of the head. The at least one implantable lead may include at least two electrode sets. Each of the at least two electrode sets may include at least two electrodes. Subcutaneously implanting the at least one implantable lead may include subcutaneously placing the at least two electrode sets near the at least two neural targets, respectively, and driving the at least two electrode sets to stimulate the at least two neural targets including at least one neural target on the left side of the head and the at least one neural target on the right side of the head.

In Example 20, the subject matter of Example 19 may optionally be configured such that subcutaneously implanting one implantable pulse generator may include implanting the one implantable pulse generator in a subcutaneous pocket superficial to the splenius capitis muscle or semispinalis capitis muscle or in a subcutaneous pocket superficial to the sternocleidomastoid muscle inferior to a mastoid process.

In Example 21, the subject matter of any one or any combination of Examples 19-20 may optionally be configured such that subcutaneously implanting at least one implantable lead may include subcutaneously implanting one lead with at least two distal branches.

In Example 22, the subject matter of any one or any combination of Example 21 may optionally be configured such that subcutaneously implanting one lead with at least two distal branches may include positioning at least two left-side branches to subcutaneously place at least two of the at least four electrode sets to at least two left-side neural targets and positioning at least two right-side branches to subcutaneously place at least two of the at least four electrode sets to at least two right-side neural targets. The at least two left-side neural targets may include at least two neural targets selected from the group consisting of: left supraorbital nerves, left temporal nerves, and left occipital nerves. The at least two right-side neural targets may include at least two neural targets selected from the group consisting of: right supraorbital nerves, right temporal nerves, and right occipital nerves.

In Example 23, the subject matter of any one or any combination of Examples 19-21 may optionally be configured to treat a migraine headache by delivering neuromodulation to one or more of a left supraorbital nerve, a right supraorbital nerve, a left temporal nerve, a right temporal nerve, a left occipital nerve and a right occipital nerve.

In Example 24, the subject matter of any one or any combination of Examples 19-21 may optionally be configured to treat a cluster headache by delivering neuromodulation to one or more of a greater occipital nerve (GON), a supraorbital nerve (SON), and a sphenopalatine ganglion (SPG).

In Example 25, the subject matter of any one or any combination of Examples 19-21 may optionally be configured to treat facial pain by delivering neuromodulation to one or more of a facial nerve and a supraorbital nerve (SON).

In one example, a neurostimulator system may include an implantable pulse generator with a processor, a driving system for driving electrodes, and a communication circuit. At least one neurostimulation lead is provided having a plurality of electrodes disposed thereon and arranged in an array on the surface thereof, and one neurostimulator and lead having a plurality of branches, each branch radiating outward with each branch having at least one array of electrodes disposed on the external surface thereof.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The following detailed description should be read with reference to the drawings. These drawings, which are not necessarily to scale, depict illustrative embodiments and are not intended to limit the scope of the invention.

Figure 1:
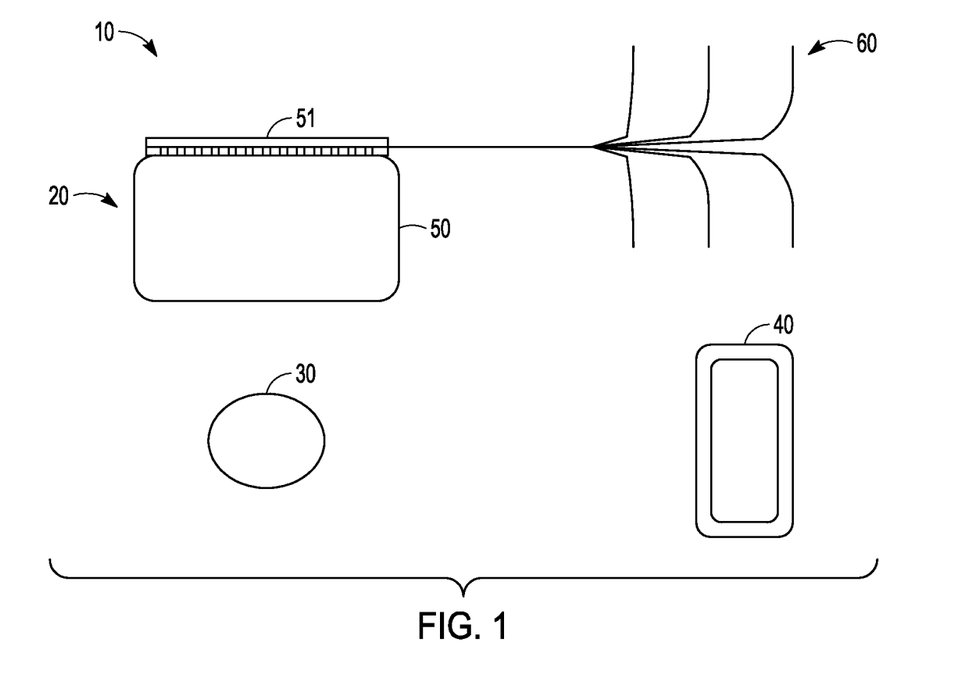
FIG. 1 illustrates, by way of example, an implanted neurostimulation system.

FIG. 1 illustrates an implanted neurostimulation system 10 including an implanted system 20, an external telemetry system and charging system 30, and a remote controller 40. The implanted system 20 may generally include an implanted pulse generator (IPG) 50, and implanted stimulation lead system 60. The IPG 50 may include a header 51 for connection with the stimulation leads 60, and a hermetically insulated housing for electronics and non-chargeable or rechargeable battery (not shown), which electronics may include a processor, a driving circuit for driving stimulation leaves and a communication circuit for communicating external to the IPG 50, a communication circuit comprising, without limitation, a near field conductive communication system. The stimulation lead(s) 60 may include a lead body with proximal connector and distal branches with nerve stimulation electrodes.

Figure 2:
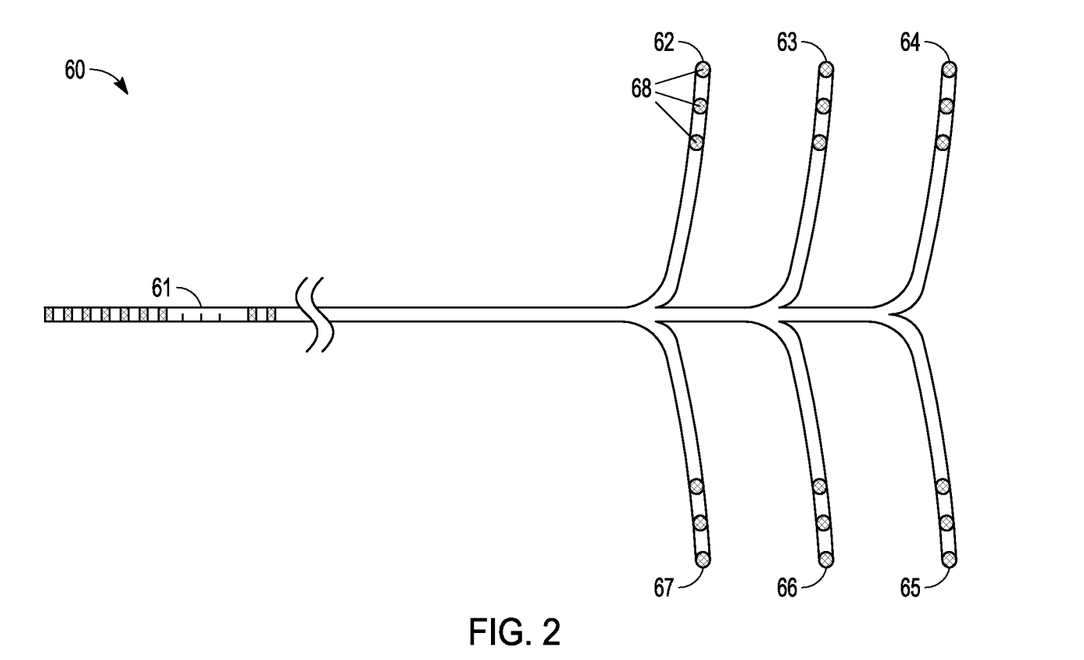
FIG. 2 illustrates, by way of example, a lead array with multiple branching leads.

FIG. 2 illustrates a stimulation lead system 60 configured to be subcutaneously implanted. By way of example and not limitation, the stimulation lead system may include six distal lead branches 62-67, which are shown schematically and not to scale. The proximal connectors 61 may include individual connectors that provide electrical connection between stimulation output channels of the IPG 50 embedded in the header 51 to the stimulation electrodes 68 on lead branch 62. Each distal lead branch may, for example, include two to three stimulation electrodes. The system may include, by way example and not limitation, 6 to 18 individual proximal connectors to provide electrical connection to the electrodes.

Figure 3:
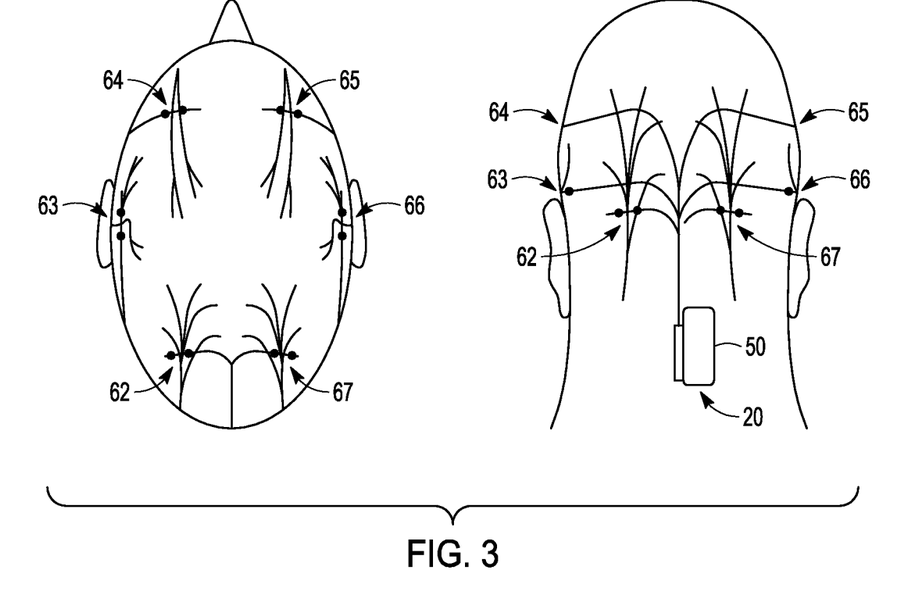
FIG. 3 illustrates, by way of example, an embodiment for subcutaneously locating the branching leads proximate to specific nerve bundles about the cranium of an individual.

FIG. 3 illustrates, by way of example and not limitation, the implanted system 20 of the IPG 50 and implanted stimulation lead system 60 subcutaneously implanted in a patient. In the illustrated embodiment, the stimulation lead system 60 with its distal lead branches 62-67 and their stimulation electrodes are subcutaneously disposed on six groups of pre-determined location of nerve branches (left and right occipital nerves, left and right temporal nerves, and left and right supraorbital nerves). The IPG 50 may be implanted in a subcutaneous pocket generally in the area superficial to the splenius capitis muscle or semispinalis capitis muscle near the upper cervical region.

Figure 4:
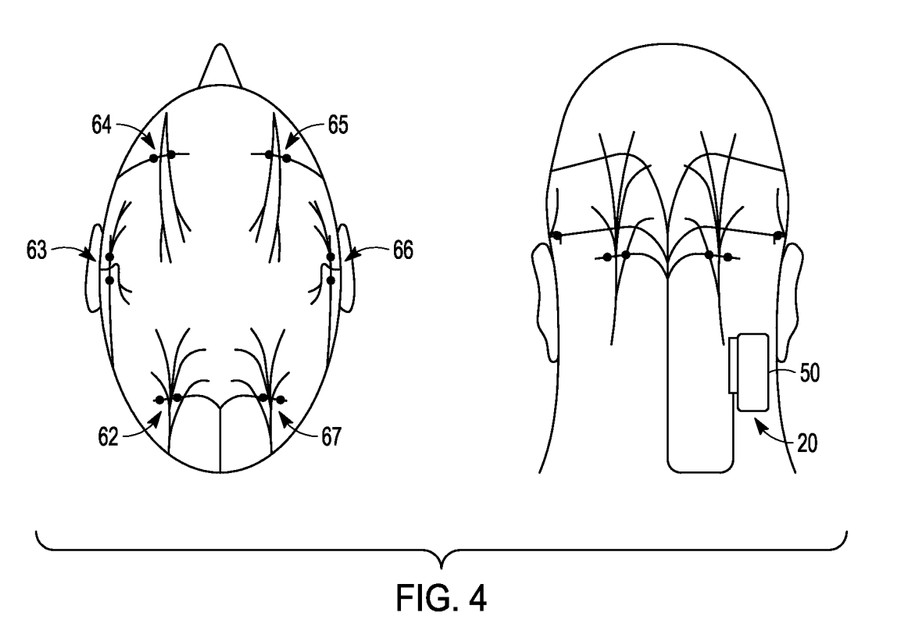
FIG. 4 illustrates, by way of example, an alternate embodiment of FIG. 3 for subcutaneous placement of the IPG.

An alternative location for the IPG 50 with lead system 60, as shown in FIG. 4, may be a subcutaneous pocket superficial to the sternocleidomastoid muscle inferior to the mastoid process. In the illustrated embodiments, the lead generally ascends along a midline of the head, providing symmetrical distribution to neural targets on the left and right side of the head.

Figure 5:
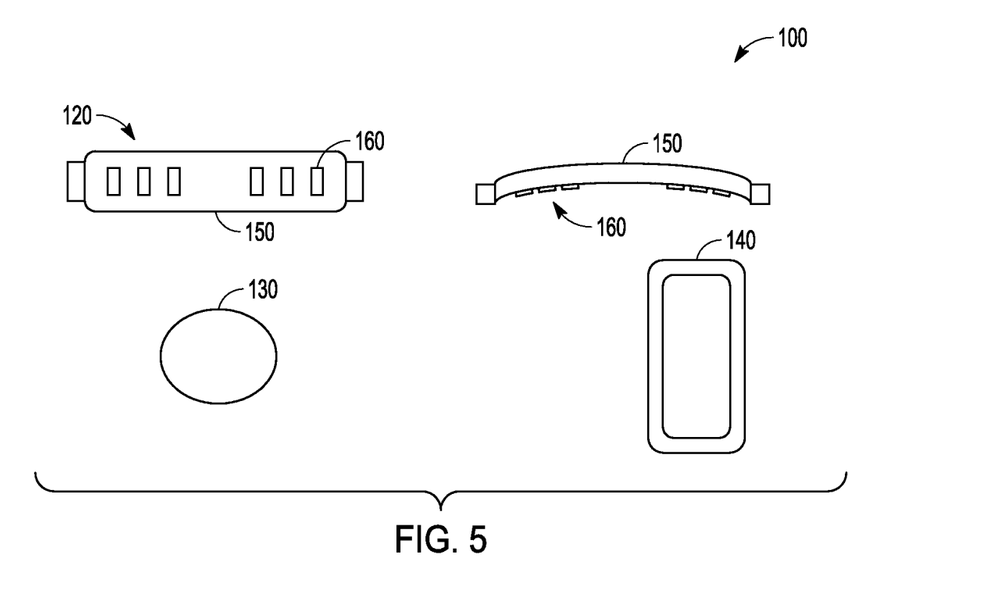
FIG. 5 illustrates, by way of example, an alternative implanted neurostimulation system.

FIG. 5 illustrates an alternative subcutaneously implanted neurostimulation system 100 including an implanted system 120, an external telemetry system and charging system 130, and remote controller 140 is shown schematically. The implanted system 120 may generally include an implanted pulse generator (IPG) 150, and stimulation electrodes 160 embedded in the housing of IPG 150. The IPG 150, insulated hermetically, contains electronics and non-chargeable or rechargeable battery and four to six stimulation electrodes 160 embedded in the housing.

Figure 6:
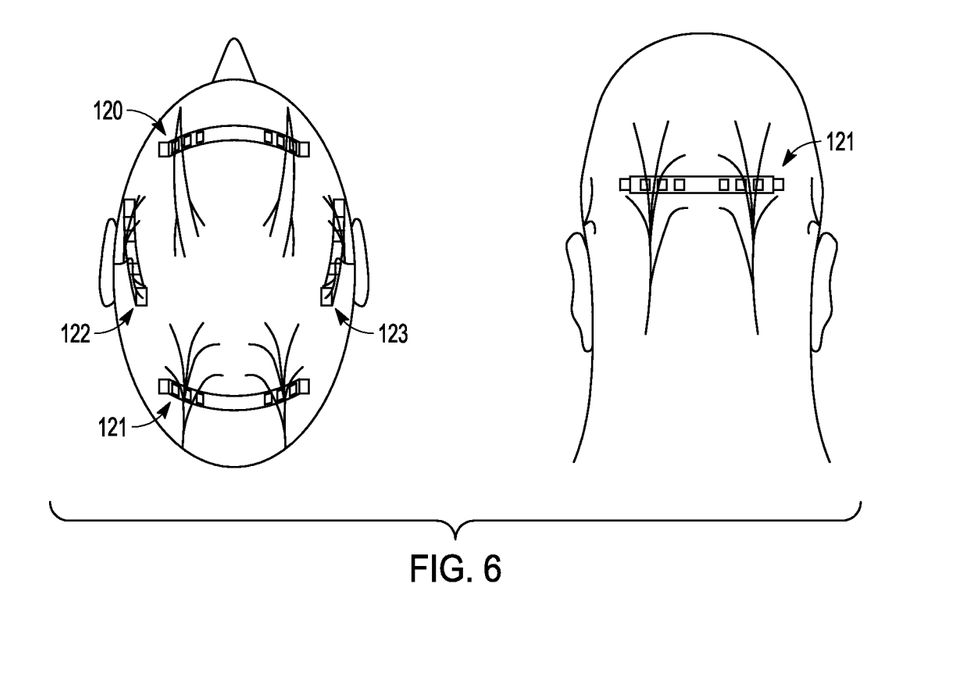
FIG. 6 illustrates, by way of example, an embodiment for subcutaneously locating the neurostimulation system of FIG. 5 about the cranium of an individual.

FIG. 6 illustrates, by way of example and not limitation, four subcutaneously implanted neurostimulation systems 100 implanted in a patient. One implanted system 120 may be placed with its stimulation electrodes disposed superficial to the left and right supraorbital nerves. One implanted system 121 may be placed with its stimulation electrode disposed superficial to the left and right occipital nerves. One implanted system 122 may be placed with its stimulation electrode disposed superficial to the left temporal nerves. One implanted system 123 may be placed with its stimulation electrode disposed superficial to the right temporal nerves.

Figure 7:
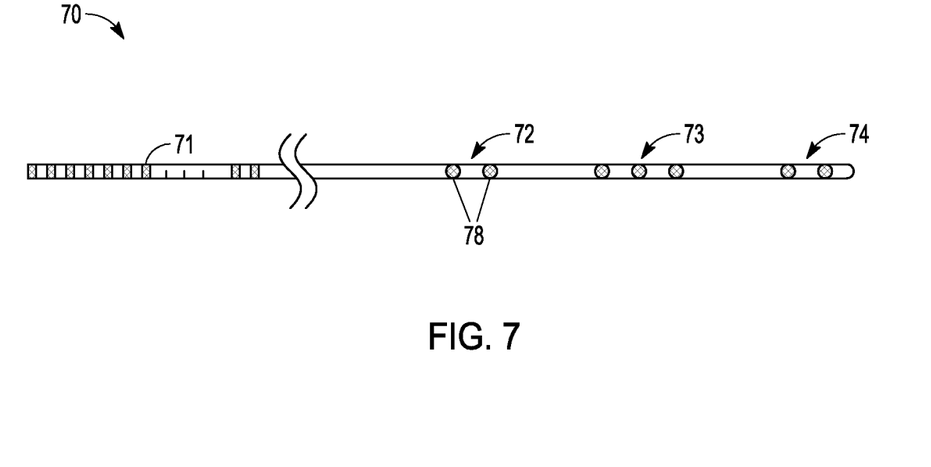
FIG. 7 illustrates, by way of example, a side view of a stimulation lead.

FIG. 7 illustrates an implanted stimulation lead system 70 including one lead body with three electrode sets or groups 72-74, which is shown schematically and not to scale. The proximal connectors 71 may include of 3 to 9 individual connectors that provide electrical connection between stimulation output channels of the IPG 50 embedded in the header 51 to the stimulation electrodes 78 as a part of electrode group 72, as illustrated at one of the electrode group and represent similar configuration for other electrode groups. Generally, each distal lead branch may include an electrode set, where the electrode set may include two to three stimulation electrodes. Each of the stimulation electrodes can function as either a cathode or anode and the IPG and be programmed to configure the electrodes as anodes, cathodes or nonfunctional electrodes, depending upon the application.

Figure 8:
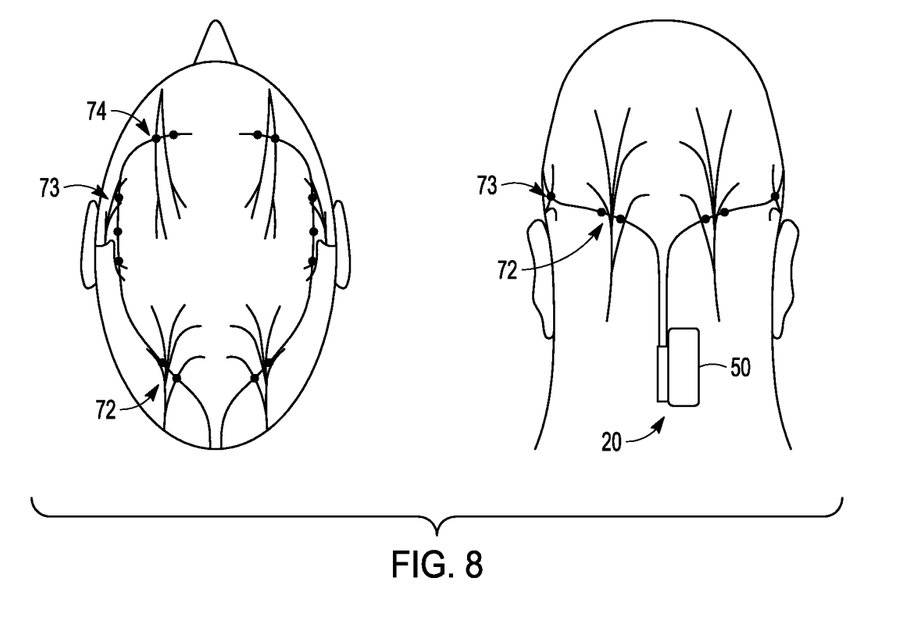
FIG. 8 illustrates, by way of example, an embodiment depicting the subcutaneous placement of the lead of FIG. 7 proximate to nerve bundles about the cranium of an individual.

FIG. 8 illustrates, by way of example and not limitation, the implanted system 20 of the IPG 50 and implanted stimulation lead system 70 subcutaneously implanted in a patient. The stimulation lead system 70 may have two leads, each with at least one electrode set or group and illustrated with three electrode sets or groups 72-74. The stimulation electrodes of each of the six electrode sets are disposed on six neural targets (e.g. nerve branches such as left and right occipital nerves, left and right temporal nerves, and left and right supraorbital nerves). The IPG 50 may be implanted in a subcutaneous pocket generally in the area superficial to the splenius capitis muscle or semispinalis capitis muscle near the upper cervical region.

Figure 9:
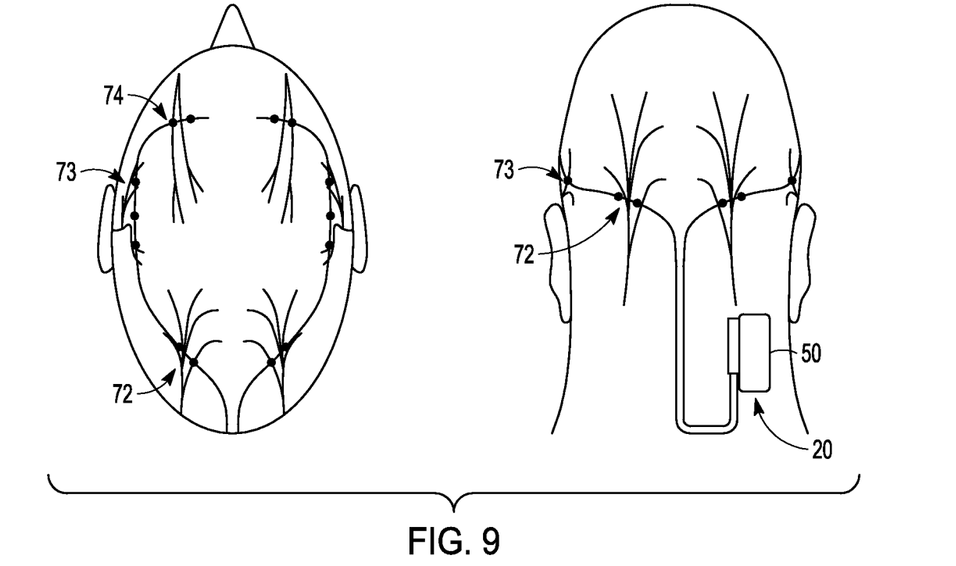
FIG. 9 illustrates, by way of example, an alternate embodiment of the subcutaneous placement of the leads of FIG. 8 with an alternate placement of the IPG.

An alternative location for the IPG 50 with lead system 70, as shown in FIG. 9, may be a subcutaneous pocket superficial to the sternocleidomastoid muscle inferior to the mastoid process.

With reference to the systems and devices depicted in FIGS. 1-4, an implanting surgeon may place the electrode sets (e.g. the distal leads 62-67 of the stimulation leads system 60) near pre-determined nerve targets (e.g., left and right supraorbital, left and right temporal, and left and right occipital nerves) through subcutaneous tunneling after making one or multiple incisions. The implanting surgeon may then make a subcutaneous pocket either superficial to the sternocleidomastoid muscle or in a more medial location that is superficial to the semispinalis capitis muscle. The surgeon may then connect the stimulation lead 60 to the IPG 50 and place them in the subcutaneous pocket.

As indicated above, left-side nerve targets may include one or more of the following nerve targets: left supraorbital nerve, left temporal nerve, and left occipital nerve. Similarly, right-side nerve targets may include one or more of the following nerve targets: right supraorbital nerve, right temporal nerve, and right occipital nerve. One or more of these nerves may be targeted to provide a therapy to treat a headache such as a migraine headache. Other therapies may be delivered, and neuromodulation may be delivered to these or other neural target(s) as may be indicated to treat various conditions. A non-exclusive example of other neural target(s) includes combinations of one or more of a greater occipital nerve (GON), a supraorbital nerve (SON), and a sphenopalatine ganglion (SPG). Modulation of one or more of these neural targets may be useful to treat cluster headaches. Another non-exclusive example includes combinations of one or more of a supraorbital nerve (SON) and a facial nerve. Modulation of one or more of these neural targets may be useful to treat facial pain. The lead(s) are designed to extend from the implantable pulse generator to enable electrode sets to be positioned at these neural target (s).

With reference to an alternative system and devices depicted in FIGS. 7-9, the implanting surgeon may place the electrode sets (e.g. groups 72-74 of the stimulation leads system 70) near pre-determined nerve targets (e.g., supraorbital, temporal, and occipital nerves) with two lead systems to cover both the left and right side of these nerves.

The patient with the implanted system 20 or a physician can adjust stimulation output parameters using the remote controller 40 through an external telemetry system 30. The patient can recharge the implanted system with a rechargeable battery using the external charging system 31.

The IPG 50 may contain hardware and firmware that deliver independent output to each stimulation electrode. The stimulation output parameters consist of amplitude, polarity, frequency, pulse width and duty cycle.

The remote controller 40 may be configured (e.g. via software, to provide a graphic user interface used to make adjustments of stimulation output parameters. The remote controller 40 also contains a stimulation algorithm from user input or through machine learning. The stimulation algorithm may include time dependent of individual setting (amplitude, polarity, frequency, pulse width and duty cycle) for each stimulation electrode.

With reference to the systems and devices depicted in FIGS. 5-6, the implanting surgeon may place implanted system 120 through an incision directly over pre-determined nerve targets (e.g., left and right supraorbital, left and right temporal, and left and right occipital nerves). The surgeon may fix the implanted system 120 on nearby fascia with the suture rings on the two ends of the IPG 150.

The patient with the implanted system 120 or a physician can adjust stimulation output parameters using the remote controller 140 through an external telemetry system, and the patient may recharge the implanted system with a rechargeable battery using the external charging system. Both the eternal telemetry system and external charging system are illustrated by an external device identified using reference number 130.

The IPG 150 may contain hardware and firmware that deliver independent output to each stimulation electrode. The stimulation output parameters may include amplitude, clarity, frequency, pulse width and duty cycle.

The remote controller 140 may contain software that provides a graphic user interface for making adjustments of stimulation output parameters. The remote controller 140 may contain a stimulation algorithm from user input or through machine learning. The stimulation algorithm may include time dependent of individual setting (amplitude, frequency, clarity, pulse width and duty cycle) for each stimulation electrode.

Figure 10:
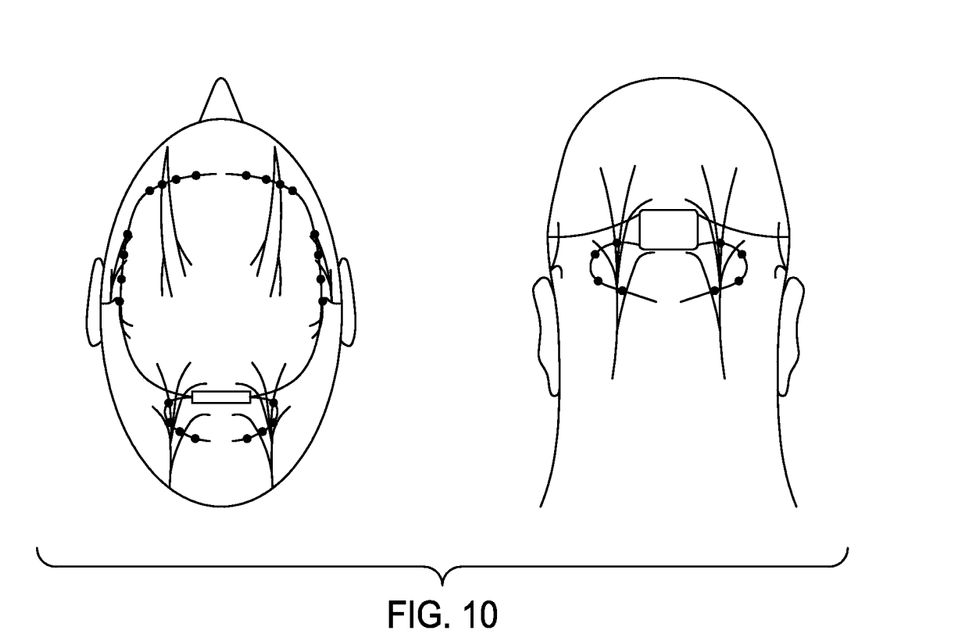
FIG. 10 illustrates, by way of example, an alternate embodiment of the subcutaneous placement of the IPG and the associated leads about the cranium of an individual.

FIG. 10 depicts embodiments that incorporate the above concepts into a single body device with no header. The lead(s) may be permanently attached to the pulse generator, and the pulse generator and lead(s) together may form a unibody construction where lead body (bodies) is (are) integrally formed with the pulse generator. For example, a lead body may be integrally formed with a housing of the pulse generator.

Although the preferred embodiment has been described in detail, it should be understood that various changes, substitutions and alterations can be made therein without departing from the spirit and scope of the invention as defined by the appended claims.

A circuit or circuitry may be implemented as part of a microprocessor circuit, which may be a dedicated processor such as a digital signal processor, application specific integrated circuit (ASIC), microprocessor, or other type of processor for processing information including physical activity information. The microprocessor circuit may be a general purpose processor that may receive and execute a set of instructions of performing the functions, methods, or techniques described herein. The circuit or circuitry may be implemented as one or more other circuits or sub-circuits that may, alone or in combination, perform the functions, methods or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified to encode instructions of the specific operation. Instructions may enable embedded hardware (e.g., the execution units or a loading mechanism) to create members of the circuit set in hardware via variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The terms "tangible" and "non-transitory," as used herein, are intended to describe a machine-readable storage medium such as a computer-readable storage medium (or "memory") excluding propagating electromagnetic signals, but are not intended to otherwise limit the type of physical computer-readable storage device that is encompassed by the phrase computer-readable medium or memory. By way of example and not limitation, a machine may include a modulation device or a programming device such as a remote control or clinician programmer. For instance, the terms "non-transitory computer readable medium" or "tangible memory" are intended to encompass types of storage devices that do not necessarily store information permanently, including for example, random access memory (RAM).

The term "machine readable medium" may include a single medium or multiple media (e.g., a centralized or distributed database, and/or associated caches and servers) configured to store instructions, and includes any medium that is capable of storing, encoding, or carrying instructions for execution by the machine and that cause the machine to perform any one or more of the techniques of the present disclosure, or that is capable of storing, encoding or carrying data structures used by or associated with such instructions. Non-limiting machine readable medium examples may include solid-state memories, and optical and magnetic media. In an example, a machine readable medium include: nonvolatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks. Program instructions and data stored on a tangible computer-accessible storage medium in non-transitory form may further be transmitted by transmission media or signals such as electrical, electromagnetic, or digital signals, which may be conveyed via a communication medium such as a network and/or a wireless link.

Method examples described herein can be machine or computer-implemented at least in part. Some examples may include a computer-readable medium or machine-readable medium encoded with instructions operable to configure an electronic device or system to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times.

Various embodiments are illustrated in the figures above. One or more features from one or more of these embodiments may be combined to form other embodiments.

The above detailed description is intended to be illustrative, and not restrictive. The scope of the disclosure should, therefore, be determined with references to the appended claims, along with the full scope of equivalents to which such claims are entitled.

What is claimed is:

1. A neurostimulator system, comprising:
one implantable pulse generator configured to be subcutaneously implanted and an implantable lead configured to extend from the subcutaneously-implanted implantable pulse generator to at least two sets of bilateral neural targets on a head, wherein the at least two sets of bilateral neural targets include a first bilateral neural target having a first left neural target on a left side of the head and a first right neural target on a right side of the head and further include a second bilateral neural target having a second left neural target on the left side of the head and a second right neural target on the right side of the head, the implantable lead including:
a lead body with proximal connectors configured to provide an electrical connection with the implantable pulse generator, wherein the lead body is configured to subcutaneously travel from the subcutaneously-implanted implantable pulse generator to the head;
at least a first set of bilateral branches extending from a first portion of the lead body and a second set of bilateral branches extending from a second portion of the lead body,
wherein:
the first set of bilateral branches correspond to the first bilateral neural target and include a first left branch configured to be subcutaneously positioned and used to stimulate the first left neural target and a first right branch configured to be subcutaneously positioned and used to stimulate the first right neural target; and
the second set of bilateral branches correspond to the second bilateral neural target and include a second left branch configured to be subcutaneously positioned and used to stimulate the second left neural target and a second right level branch configured to be subcutaneously positioned and used to stimulate the second right neural target,
wherein the first portion of the lead body from which the first set of bilateral branches extend is closer to the proximal connectors than the second portion of the lead body from which the second set of bilateral branches extend,
wherein each of the branches in both the first set of bilateral branches and the second set of bilateral branches includes a distal branch portion with a set of electrodes, and
wherein the implantable pulse generator and the implantable lead are configured to electrically stimulate each of the first bilateral neural target and the second bilateral neural target.

2. The neurostimulator system of claim 1, wherein the implantable pulse generator is configured for implantation in a subcutaneous pocket superficial to a splenius capitis muscle or a semispinalis capitis muscle or in a subcutaneous pocket superficial to a sternocleidomastoid muscle inferior to a mastoid process.

3. The neurostimulator system of claim 1, wherein the at least two sets of bilateral neural targets include bilateral neural targets selected from the group consisting of:
left and right supraorbital nerves,
left and right temporal nerves, and
left and right occipital nerves.

4. The neurostimulator system of claim 1, wherein the at least two sets of bilateral neural targets include three bilateral neural targets, and the three bilateral neural targets include:
left and right supraorbital nerves,
left and right temporal nerves, and
left and right occipital nerves.

5. The neurostimulator system of claim 1, wherein the at least two sets of bilateral neural targets include bilateral neural targets selected from the group consisting of: a greater occipital nerve (GON), a supraorbital nerve (SON), and a sphenopalatine ganglion (SPG); or a facial nerve.

6. The neurostimulator system of claim 1, wherein the set of electrodes of the distal branch portion for each of the branches in the first set of bilateral branches and in the second set of bilateral branches includes at least two electrodes.

7. The neurostimulator system of claim 6, wherein the set of electrodes of the distal branch portion for each of the branches in the first set of bilateral branches and in the second set of bilateral branches includes three electrodes.

8. The neurostimulator system of claim 1, wherein a total number of electrodes in the first left branch, the first right branch, the second left branch, and the second right branch correspond to a number of proximal connectors, and the implantable pulse generator is configured to independently control stimulation from each of the total number of electrodes.

9. The neurostimulator system of claim 1, wherein the second portion from which the second set of bilateral branches extend is at a distal end of the lead body.

10. The neurostimulator system of claim 1, wherein:
the at least two sets of bilateral neural targets on the head include a third bilateral neural target having a third left neural target on the left side of the head and a third right neural target on the right side of the head,
the implantable lead includes a third set of bilateral branches extending from a third portion of the lead body, and the third set of bilateral branches correspond to the third bilateral neural target and include a third left branch configured to be subcutaneously positioned and used to stimulate the third left neural target and a third right branch configured to be subcutaneously positioned and used to stimulate the third right neural target.

11. The neurostimulator system of claim 10, wherein:
the first left branch and the first right branch have equal lengths, the second left branch and the second right branch have equal lengths, and the third left branch and the third right branch have equal lengths; and
the first set of bilateral branches has different lengths compared to both the second set of bilateral branches and the third set of bilateral branches, and the second set of bilateral branches has different lengths compared to the third set of bilateral branches.

12. A method, comprising:
subcutaneously implanting an implantable pulse generator and subcutaneously implanting an implantable lead, the implantable lead being configured to extend from the implantable pulse generator to at least two sets of bilateral neural targets on a head, wherein the at least two sets of bilateral neural targets include a first bilateral neural target having a first left neural target on a left side of the head and a first right neural target on a right side of the head and further include a second bilateral neural target having a second left neural target on the left side of the head and a second right neural target on the right side of the head, the implantable lead including:
a lead body with proximal connectors configured to provide an electrical connection with the implantable pulse generator, wherein the lead body is configured to subcutaneously travel from the subcutaneously-implanted implantable pulse generator to the head;
at least a first set of bilateral branches extending from a first portion of the lead body and a second set of bilateral branches extending from a second portion of the lead body, wherein:
the first set of bilateral branches correspond to the first bilateral neural target and include a first left branch configured to be subcutaneously positioned and used to stimulate the first left neural target and a first right branch configured to be subcutaneously positioned and used to stimulate the first right neural target; and
the second set of bilateral branches correspond to the second bilateral neural target and include a second left branch configured to be subcutaneously positioned and used to stimulate the second left neural target and a second right level branch configured to be subcutaneously positioned and used to stimulate the second right neural target,
wherein the first portion of the lead body from which the first set of bilateral branches extend is closer to the proximal connectors than the second portion of the lead body from which the second set of bilateral branches extend, and
wherein each of the branches in both the first set of bilateral branches and the second set of bilateral branches includes a distal branch portion with a set of electrodes; and electrically connecting the one implantable pulse generator to the proximal connectors of the lead body, wherein the implantable pulse generator and the implantable lead are configured to electrically stimulate each of the first bilateral neural target and the second bilateral neural target.

13. The method of claim 12, wherein the at least two sets of bilateral neural targets include bilateral neural targets selected from the group consisting of:
left and right supraorbital nerves,
left and right temporal nerves, and
left and right occipital nerves.

14. The method of claim 12, wherein implanting the at least one implantable pulse generator includes implanting the at least one implantable pulse generator in a subcutaneous pocket superficial to a splenius capitis muscle or a semispinalis capitis muscle or in a subcutaneous pocket superficial to a sternocleidomastoid muscle inferior to a mastoid process.

15. The method of claim 12, wherein the set of electrodes of the distal branch portion for each of the branches in the first set of bilateral branches and in the second set of bilateral branches includes at least two electrodes, and subcutaneously implanting the implantable lead includes subcutaneously tunneling the distal branch portion to operably position the at least two electrodes to stimulate a corresponding neural target.

16. The method of claim 15, wherein the set of electrodes of the distal branch portion for each of the branches in the first set of bilateral branches and in the second set of bilateral branches includes three electrodes.

17. The method of claim 16, wherein a total number of electrodes in the first left branch, the first right branch, the second left branch, and the second right branch correspond to a number of proximal connectors, and the method further includes using the implantable pulse generator to independently control stimulation from each of the total number of electrodes.

18. The method of claim 12, wherein the second portion from which the second set of bilateral branches extend is at a distal end of the lead body.

19. The method of claim 12, wherein:
the at least two sets of bilateral neural targets on the head include a third bilateral neural target having a third left neural target on the left side of the head and a third right neural target on the right side of the head,
the implantable lead includes a third set of bilateral branches extending from a third portion of the lead body, and
the third set of bilateral branches correspond to the third bilateral neural target and include a third left branch configured to be subcutaneously positioned and used to stimulate the third left neural target and a third right branch configured to be subcutaneously positioned and used to stimulate the third right neural target.

20. The method of claim 19, wherein:
the first left branch and the first right branch have equal lengths, the second left branch and the second right branch have equal lengths, and the third left branch and the third right branch have equal lengths; and
the first set of bilateral branches has different lengths compared to both the second set of bilateral branches and the third set of bilateral branches, and the second set of bilateral branches has different lengths compared to the third set of bilateral branches.

* * * * *

UNITED STATES PATENT AND TRADEMARK OFFICE
CERTIFICATE OF CORRECTION

| | | |
|---|---|---|
| PATENT NO. | : 12,343,522 B2 | Page 1 of 1 |
| APPLICATION NO. | : 17/434161 | |
| DATED | : July 1, 2025 | |
| INVENTOR(S) | : Mudit K. Jain | |

It is certified that error appears in the above-identified patent and that said Letters Patent is hereby corrected as shown below:

In the Claims

In Column 12, Line 1, in Claim 1, after "right", delete "level"

In Column 13, Line 50, in Claim 12, after "right", delete "level"

In Column 13, Line 61, in Claim 12, after "and", insert a linebreak

Signed and Sealed this
Nineteenth Day of August, 2025

Coke Morgan Stewart
*Acting Director of the United States Patent and Trademark Office*